United States Patent
Rosenstatter

[11] Patent Number: 6,030,216
[45] Date of Patent: Feb. 29, 2000

[54] DENTISTRY HAND PIECE

[76] Inventor: Otto Rosenstatter, Matzing 105, A-5164 Seeham, Austria

[21] Appl. No.: 09/105,851

[22] Filed: Jun. 29, 1998

[30] Foreign Application Priority Data

Jul. 2, 1997 [AT] Austria ................................. 1133/97

[51] Int. Cl.⁷ ..................................................... A61C 1/07
[52] U.S. Cl. .......................... 433/120; 122/124; 122/118
[58] Field of Search ..................... 433/118, 122, 433/123, 124, 120, 142, 128, 127

[56] References Cited

U.S. PATENT DOCUMENTS

| | | | |
|---|---|---|---|
| 2,917,829 | 12/1959 | Page | 433/127 |
| 3,098,299 | 7/1963 | Page | 433/127 |
| 4,175,324 | 11/1979 | Arai | 433/122 |
| 4,330,282 | 5/1982 | Nash | 433/118 |
| 4,483,676 | 11/1984 | Thierman | 433/142 |
| 4,484,892 | 11/1984 | Pernot et al. | 433/118 |
| 4,484,893 | 11/1984 | Finn | 433/118 |
| 4,690,642 | 9/1987 | Kyotani | 433/142 |
| 4,781,589 | 11/1988 | Bareth | 433/122 |
| 4,840,566 | 6/1989 | Leonard | 433/127 |
| 4,940,410 | 7/1990 | Apap et al. | 433/102 |
| 5,059,122 | 10/1991 | Hetzel | 433/118 |
| 5,118,291 | 6/1992 | Varaine | 433/142 |
| 5,133,661 | 7/1992 | Euvrard | 433/120 |
| 5,158,457 | 10/1992 | Meier et al. | 433/118 |
| 5,431,565 | 7/1995 | Euvrard | 433/119 |
| 5,454,718 | 10/1995 | Strohmaier | 433/122 |
| 5,797,743 | 8/1998 | Bailey | 433/126 |

FOREIGN PATENT DOCUMENTS

| | | |
|---|---|---|
| 379 505 | 1/1986 | Austria . |
| 34 17 123 | 11/1985 | Germany . |
| 35 40 621 | 5/1987 | Germany . |
| 96/14024 | 5/1996 | WIPO . |

Primary Examiner—Jeffrey A. Smith
Attorney, Agent, or Firm—Wenderoth, Lind & Ponack, L.L.P.

[57] ABSTRACT

A dentistry hand piece is provided wherein a rotation of a drive motor is converted into an oscillation of a receiving part for a dentistry tool. The conversion of the rotation into the oscillation takes place in an attachment head (3) of the hand piece. The longitudinal axis (51) of the receiving part (8, 8') for the tool in the attachment head (3) is arranged at an angle (preferably approximately at right-angles) to the longitudinal axis (53) of the neck area (1) of the hand piece adjoining the attachment head (3), and the plane of oscillation of the receiving part (8, 8') for the tool is substantially perpendicular to the longitudinal axis (51) of the receiving part (8, 8').

18 Claims, 6 Drawing Sheets

DENTISTRY HAND PIECE

BACKGROUND OF THE INVENTION

The invention relates to a dentistry hand piece, wherein a rotation of a drive motor is converted into an oscillation of a receiving part for a dentistry tool.

Such a hand piece is known, for example, from U.S. Pat. No. 5,133,661. In this straight hand piece, an eccentric driven by a rotating drive shaft is provided, which causes a receiving part for a tool to oscillate. The receiving part arranged in the shaft of the hand piece, in the longitudinal direction of the hand piece, is provided at its forward end with a thread into which the tool can be screwed. Instead of a tool, an attachment head can also be screwed into the thread, which then oscillates as a whole in operation and which is provided with a chuck for inserting a vibrating tool.

Modifications must be made in order to obtain suitably practical ergonomics of the hand piece, so that the places to be treated on the teeth can be reached with the tip of the tool fitted into the receiving part or in the attachment head. On one hand, the tools which can be screwed into the receiving part are bent, wherein their tips are at an angle to the longitudinal axis of the hand piece. On the other hand, the chuck of the attachment head which can be screwed into the receiving part is arranged at an angle to the longitudinal axis of the hand piece. However, when this is done the plane of oscillation of the tool is inclined with respect to the forward area of the tool, and the movement of the tip of the tool has a disadvantageous "knocking" component (component of movement directed perpendicular to the surface of the tooth) during various types of treatment when it is placed on the tooth.

SUMMARY OF THE INVENTION

The object of this invention is to provide an improved dentistry hand tool of the general type described in the introduction. In accordance with the invention, this tool is provided so that the conversion of rotation into oscillation takes place in an attachment head of the hand piece, wherein the longitudinal axis of the receiving part for the tool, arranged in the attachment head, is at an angle (preferably at right-angles) to the longitudinal axis of the neck area (or portion) of the hand piece connected to the attachment head. Furthermore, the plane of oscillation of the receiving part for the tool is substantially perpendicular to the longitudinal axis of the receiving part.

An important advantage of this hand piece is that in the case of insertion of a straight tool into the receiving part, advantageous ergonomics of the hand tool are achieved. In addition, a plane of oscillation of the tip of the tool is obtained which is perpendicular to the longitudinal axis of the tool, so that when it is placed on the tooth, it does not result in any knocking movement component directed against the surface of the tooth.

These two requirements cannot be satisfied at the same time with the hand piece according to U.S. Pat. No. 5,133,661.

Further, the hand piece according to the invention provides for different attachment heads for vibrating and rotating tools to be coupled to the hand piece alternatively by means of a quick release lock. Therefore, a universal hand piece is produced in a simple manner.

BRIEF DESCRIPTION OF THE DRAWINGS

Further advantages and details of the invention will be explained hereinafter with reference to the attached drawings, in which.

DETAILED DESCRIPTION OF THE INVENTION

Figure 1:
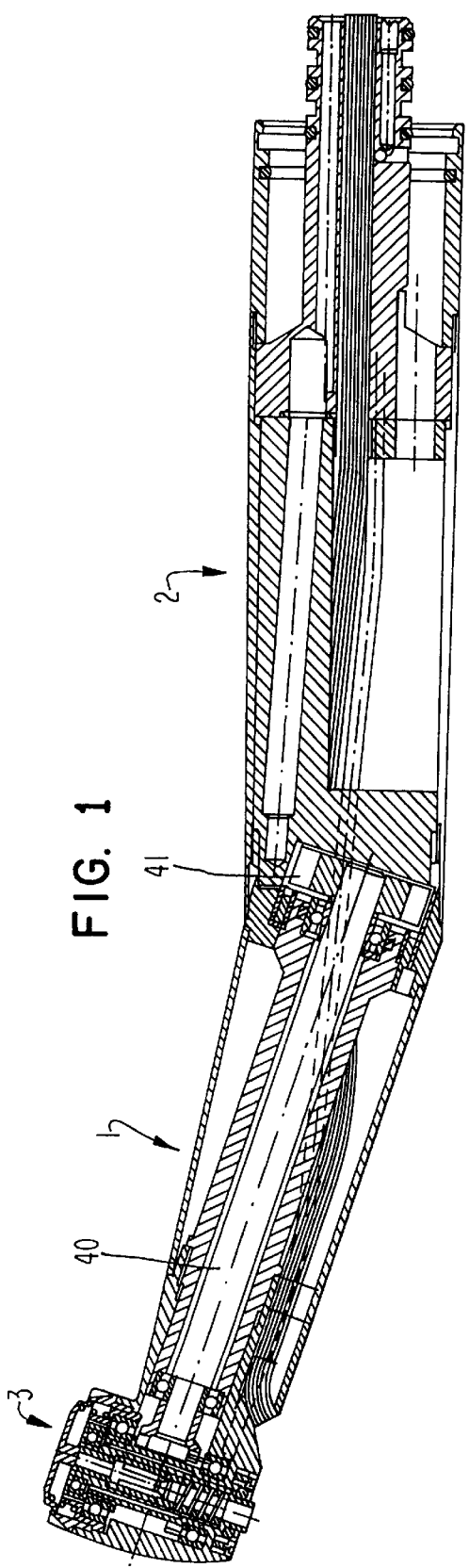
FIGS. 1 and 2 are longitudinal sections through two hand pieces according to the invention.

The hand piece shown in FIG. 1 is provided with a neck portion 1 and a handle area 2, which are arranged at an angle to one another. An attachment head 3 can be fitted to the neck portion 1, by, for example, a screw connection or a snap fitting. The handle portion 2 of the hand piece can be connected by a connector (which is not shown) to a supply line. A shaft 40 is arranged in the neck portion 1, and is driven by a compressed air-driven turbine 41 arranged coaxially with respect to the shaft 40.

Figure 2:
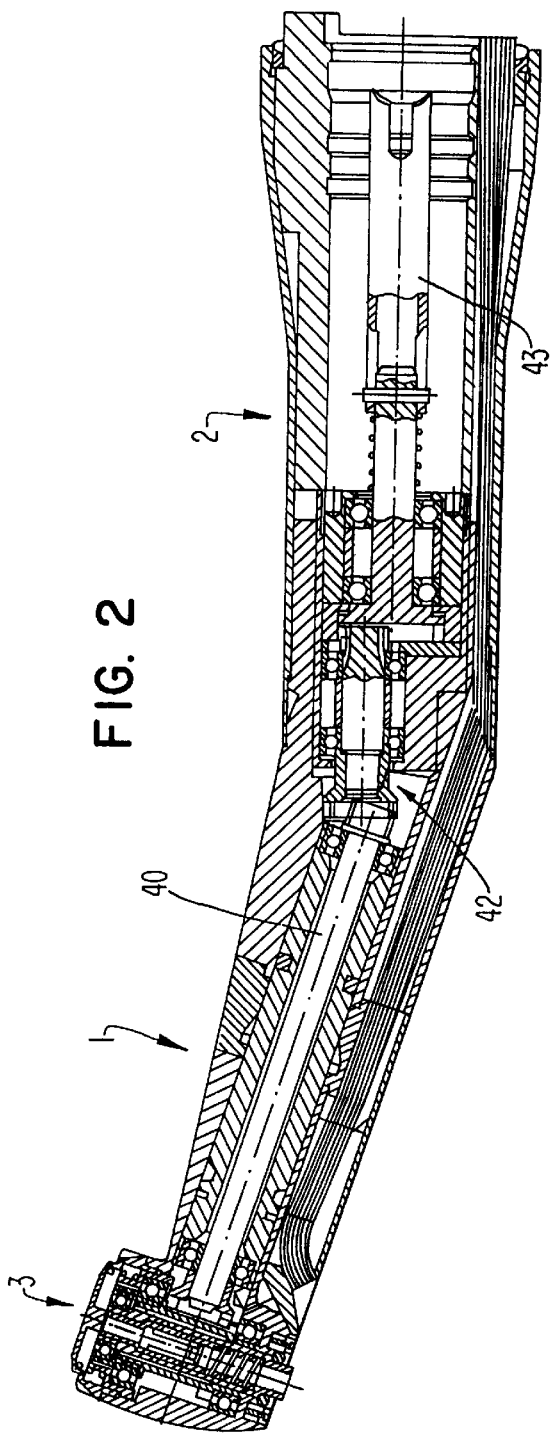

In the hand piece shown in FIG. 2, the shaft 40 in the neck portion 1 of the hand piece is joined by an angle transforming gear 42 to a shaft 43 running through the handle portion 2. Shaft 43 is driven by an electric motor in a motor part (which is not shown) which can be connected to the handle portion 2 and is rotatably connected to a supply line.

Figure 3:
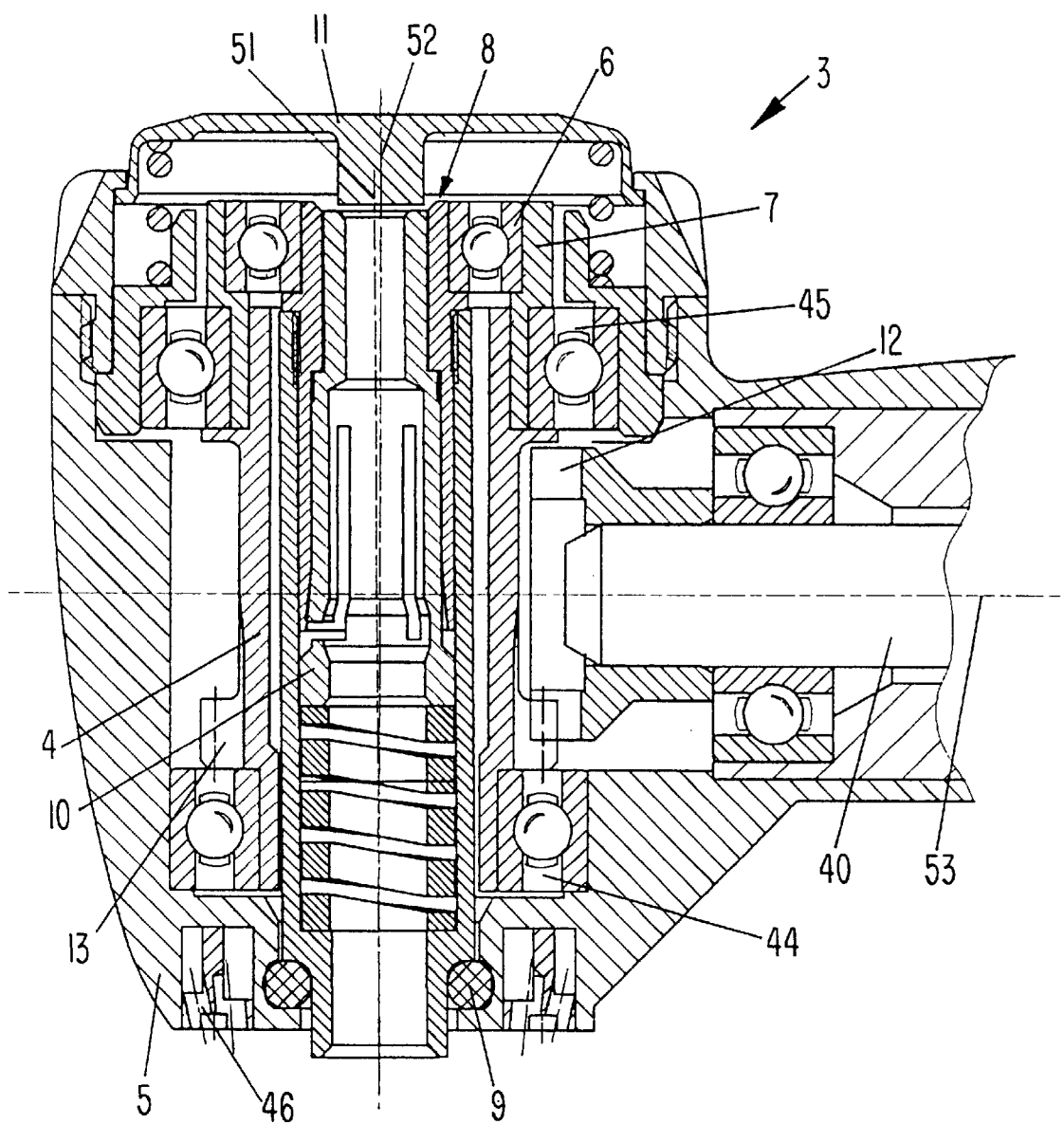
FIG. 3 is an enlarged diagram of the attachment head of the hand pieces of FIGS. 1 and 2.

In the case of both of the hand pieces shown in FIGS. 1 and 2, an attachment head can be used which is configured in completely the same manner (apart from its parts for connection to the neck portion 1 of the hand piece). This attachment head is shown more precisely in FIG. 3.

In the housing 5 of the attachment head a receiving part 8 for a dentistry tool is provided. This receiving part 8 comprises a conventional, spring-loaded chuck 10. By actuation of the knob 11 arranged on the rear of the attachment head, the chuck 10 is opened and a tool can be fitted into the chuck 10 or removed therefrom.

The rotation of the drive shaft 40 projecting into the attachment head (drive member) is converted by a corner gear formed by the toothed wheels 12 and 13 into a rotation of the bearing sleeve 4 which is rotatably mounted by means of ball bearings 44, 45 in the housing 5 of the attachment head 3. The bearing sleeve 4 is connected in a non-rotatable manner to the eccentric 7, which is configured as a sleeve with an eccentric circular bore. The ball bearing 6 thus sits eccentrically in this bore, in which in turn a rear area of the receiving part 8 is arranged. By rotation of the eccentric 7, which forms a forced guide for the receiving part, the rear area of the receiving part 8 is made to oscillate, which can be transferred via the chuck 10 to a tool fitted into the receiving part. The forward area of the receiving part 8 is mounted in the housing 5 of the attachment head by means of an elastic element, preferably an O-ring 9. This O-ring 9 on the one hand protects the receiving part 8 from rotating with respect to the housing 5, and on the other hand forms an oscillation bearing. The rotation speed of the bearing sleeve 4 is selected (preferably in the range of up to 300,000 r.p.m.) such that the receiving part 8 is caused to oscillate together with the tool fitted into the chuck 10 of the receiving part 8, wherein a nodal point occurs at the site of the O-ring 9. The plane of this oscillation is therefore substantially perpendicular to the longitudinal axis 51 of the receiving part 8 (i.e., there is no "swinging" movement). Consequently, the eccentric 7 oscillates the receiving part 8 such that the front end of a tool inserted in the receiving part oscillates in a circular trajectory which lies in a plane perpendicular to the longitudinal axis of the receiving part.

Because of the mounting of the receiving part 8 in the eccentric 7, with the eccentric 7 being set with respect to the longitudinal axis 52 of the attachment head, the longitudinal axis 51 of the receiving part 8 is inclined by a small angle. This angle is preferably in the range of less than ten (10) degrees. Particularly good ergonomics of the hand piece are produced when the angle between the longitudinal axis 51 of the receiving part and the longitudinal axis 53 of the neck portion 1 of the hand piece (the exact value of which naturally varies slightly with the setting of the eccentric 7) is approximately 90°.

In the forward area of the attachment head 3, there are provided apertures 46 for a spray for cooling the tool and respectively the tooth surface being treated.

Figure 4:
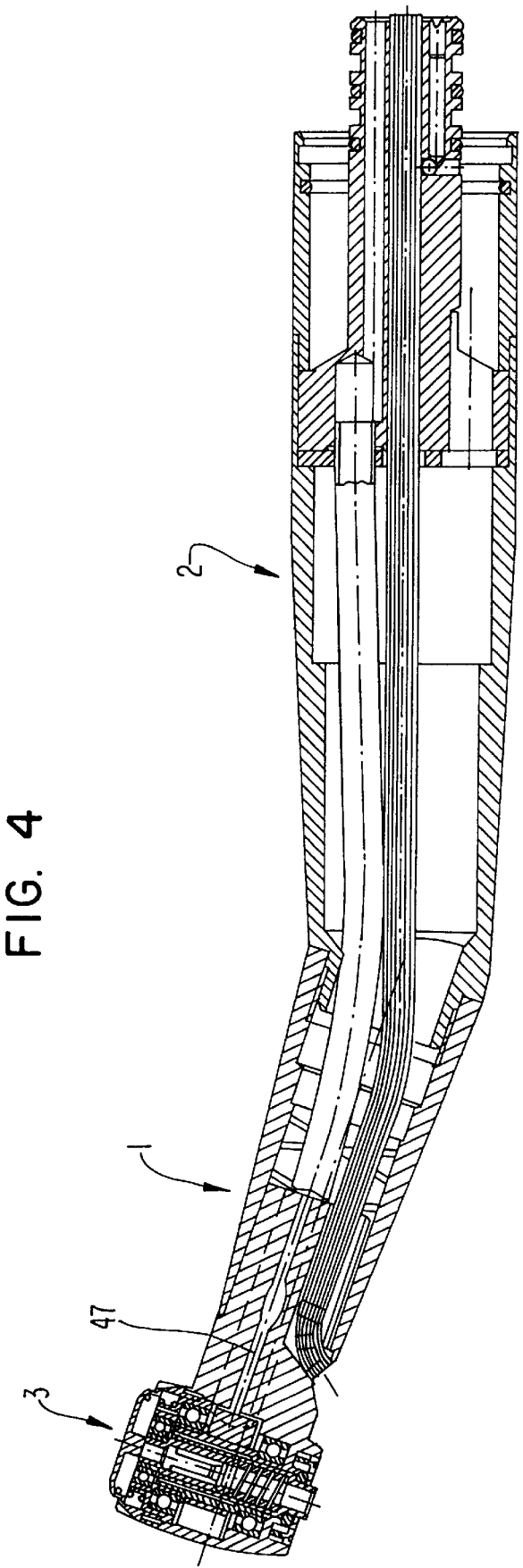
FIG. 4 is a longitudinal section through a further hand piece according to the invention.
Figure 5:
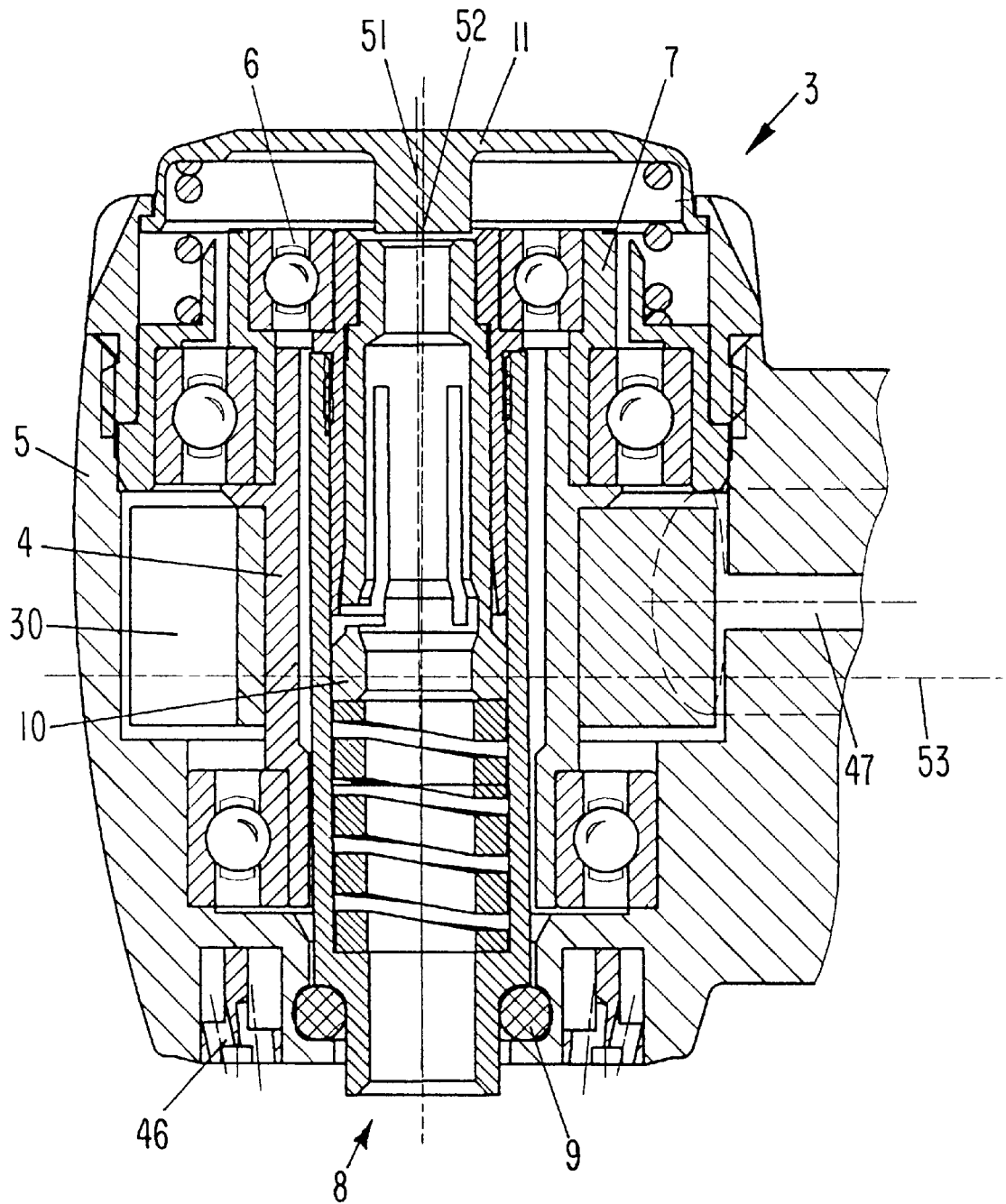
FIG. 5 is an enlarged diagram of the attachment head of the hand piece of FIG. 4.

A further dentistry hand piece, in which a drive member comprising a drive motor configured as a compressed air-driven turbine is arranged directly in the treatment (attachment) head 3, is shown in FIGS. 4 and 5. This turbine is provided with a turbine impeller 30 against which an air stream flows through the air channel 47. The turbine impeller 30 sits directly on the bearing sleeve 4 which is consequently made to rotate by means of the turbine impeller. The further construction of the treatment head 3 is completely analogous to that of the treatment head shown in FIG. 3 and therefore does not need to be described further.

An eccentric could, in principle, also be constructed in a manner different than that described. For example, a driven, not absolutely rotationally symmetrical, cam can act upon the receiving part and cause it to oscillate or vibrate.

Figure 6:
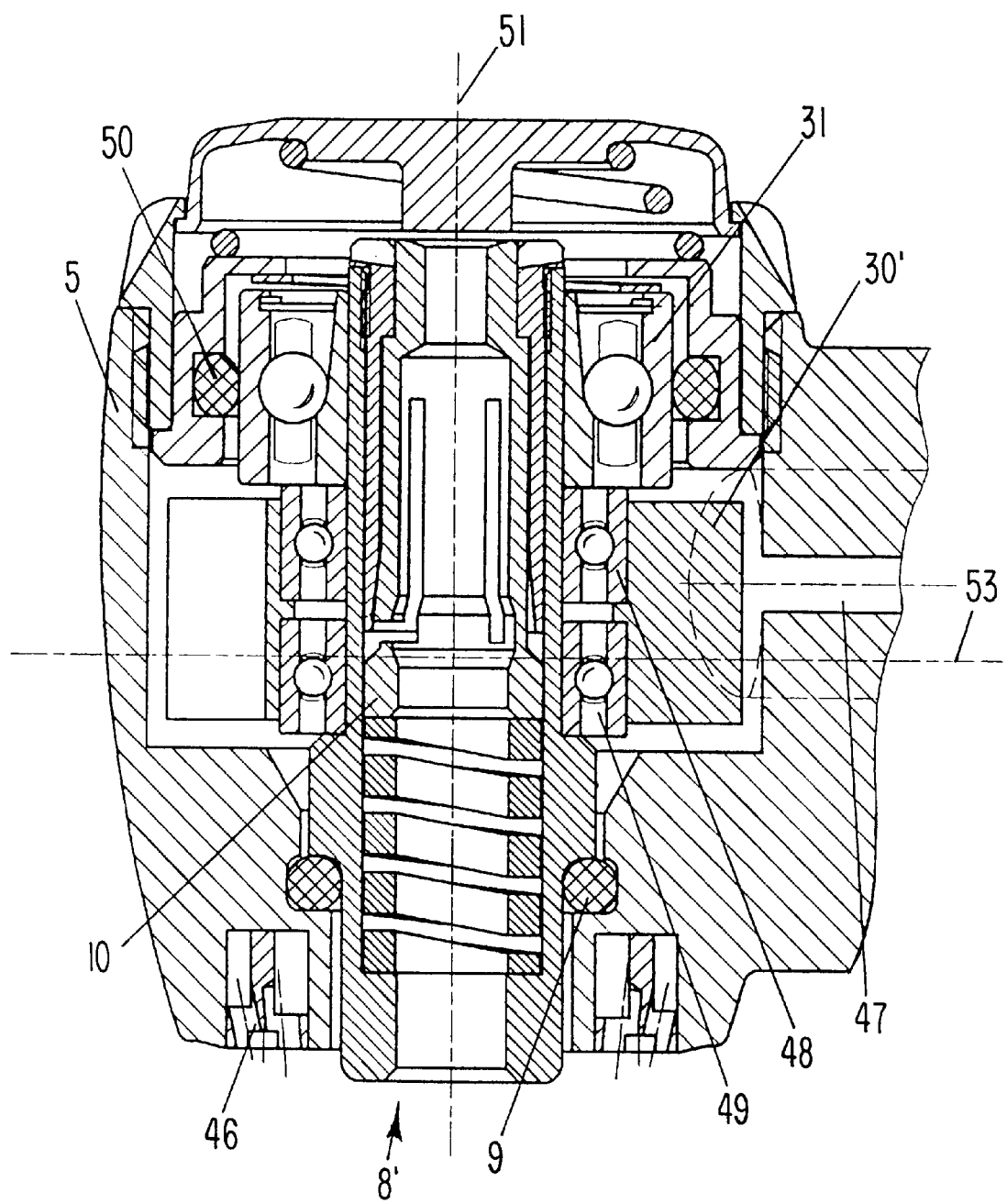
FIG. 6 is a further embodiment of an attachment head according to the invention.

FIG. 6 shows a further attachment head, which is alternatively suitable to the attachment head shown in FIG. 5 for use with the hand piece according to FIG. 4. This attachment head is also provided with a turbine with an impeller 30' to which air is applied. This is mounted directly by means of ball bearings 48, 49 on the receiving part 8'. The receiving part 8' is mounted in a non-rotatable but elastic manner in the housing 5 of the treatment head. Additionally, in its forward area it is mounted by means of an O-ring 9 and in its rear area by means of a ball bearing 31 and a further elastic element in the form of an O-ring 50 in the housing 5. The arrangement of the ball bearing 31 and the O-ring 50 can also be changed around, so that the O-ring 50 externally follows the receiving part 8' and externally following this the ball bearing 31 is arranged. Since the impeller 30' is unbalanced (has a slightly asymmetrical weight distribution), during its rotation it causes the receiving part 8' to oscillate. The ball bearing 31 serves to take up the rolling movement occurring around the vibration bearing 9 during the oscillation. Thereby, it prevents excessive stressing of the O-ring 50 which would otherwise take place. The speed of rotation of the impeller 30' can again be in the range of up to 300,000 r.p.m.

Instead of the impeller 30, which is unbalanced, an unbalanced part driven by a shaft and a gear could, in principle, also be provided.

Figure 7:
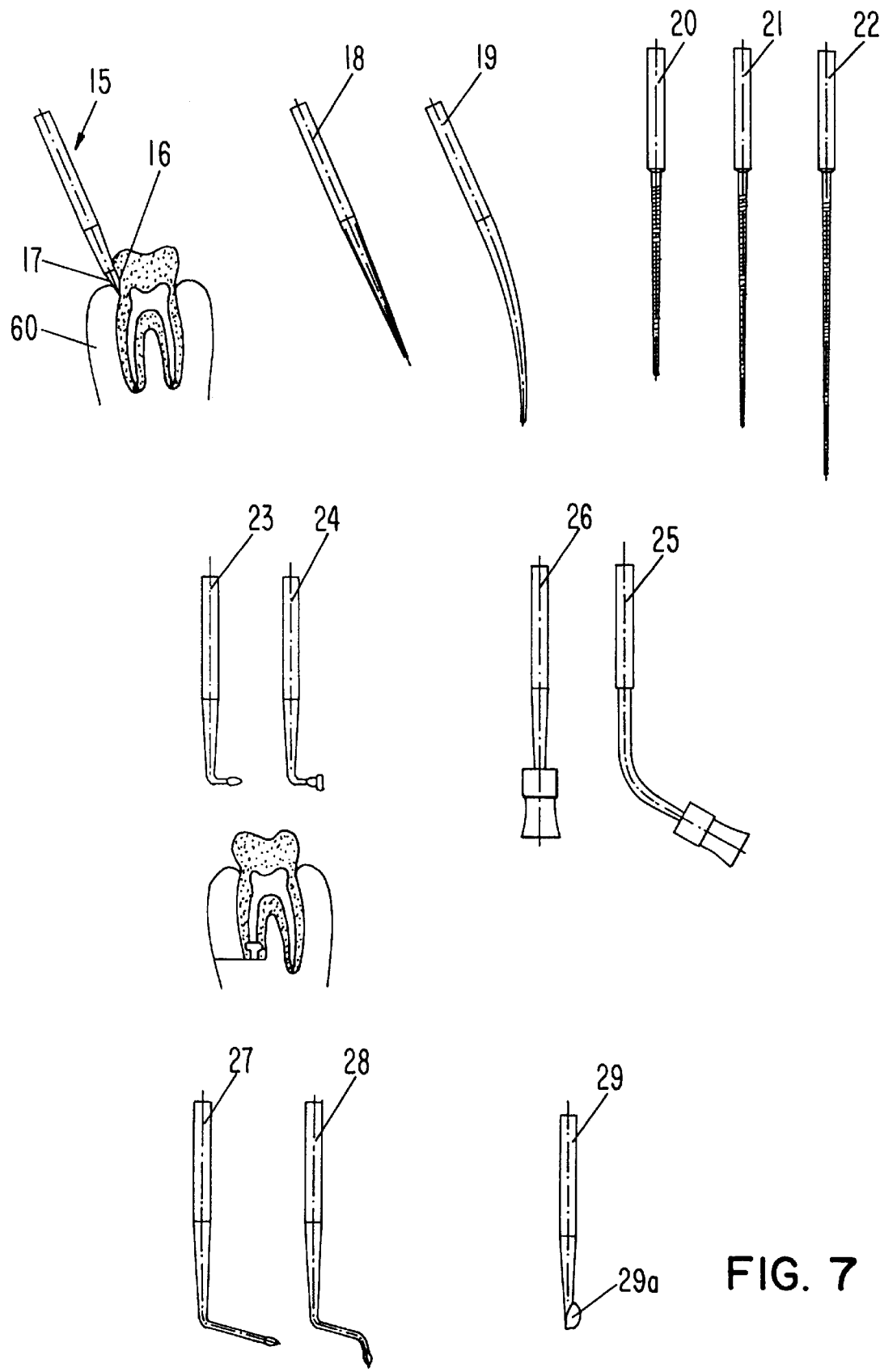
FIG. 7 is a view of different tools which are suitable for use with a hand piece according to the invention.

In FIG. 7 different treatment tools are shown schematically, which are suitable for different types of treatment using the dentistry hand pieces according to the invention. The tool 15 is provided with a working area, the front side of which is provided with an abrasive surface 16 for polishing the tooth, and rear side of which has a polished surface 17 to prevent damage to the gums 60 when the teeth are polished under the gums 60. For this purpose, the surface 17 is further flattened and, moreover, is distinguished by color so that the dentist has a better opportunity for checking visually.

Different shapes of tools 18, 19 are provided for preparation using the scaler. For preparatory treatment of the root canal, different filing instruments 20, 21, 22 are provided. The oscillating inserts 23, 24 are used for retrograde root canal preparation. Brush inserts 25, 26 are provided for gentle removal of plaque. For mechanical root surface work in the area of furcation, oscillating instruments 27, 28 are provided. For preparation of small cavities in the interdental region, without damaging the adjacent tooth, the oscillating insert 29 is provided on one side with a diamond surface 29a.

I claim:

1. A dentistry hand piece comprising:
   a neck portion having a longitudinal axis;
   an attachment head connected to said neck portion, said attachment head including a receiving part for receiving a tool, a rotatable drive member, and a rotation converter for converting said rotation of said drive member into an oscillation of said receiving part, said rotation converter including an eccentric driven by said drive member, said eccentric forming a forced guide for oscillating said receiving part such that a front end of the tool, when the tool is received by said receiving part, oscillates in a circular trajectory lying in a plane perpendicular to a longitudinal axis of said receiving part; and
   wherein an angle is formed between the longitudinal axis of said receiving part and the longitudinal axis of said neck portion.

2. The hand piece of claim 1, wherein the angle formed between the longitudinal axis of said receiving part and the longitudinal axis of said neck portion is substantially perpendicular.

3. The hand piece of claim 2, wherein said attachment head is removably connected to said neck portion.

4. The hand piece of claim 1, further comprising a handle portion having a longitudinal axis, wherein said handle portion is connected to said neck portion such that an angle is formed between the longitudinal axis of said neck portion and the longitudinal axis of said handle portion.

5. The hand piece of claim 1, wherein said receiving part has a chuck forming a quick release lock for a tool.

6. The hand piece of claim 5, wherein said attachment head includes a push button to actuate said chuck for insertion and removal of the tool.

7. The hand piece of claim 1, wherein said attachment head further includes a housing and an elastic element for mounting said receiving part, said elastic element being provided in a forward portion of said housing.

8. The hand piece of claim 1, wherein said drive member comprises a portion of a longitudinal drive shaft extending from said neck portion into said attachment head, said drive member further comprising a direction changing gear for transferring a rotation from said drive shaft to said eccentric.

9. The hand piece of claim 8, further comprising a drive motor, said drive motor being a compressed air-driven turbine arranged coaxially with respect to said drive shaft.

10. The hand piece of claim 1, wherein said receiving part has a rear end, said eccentric forming a forced guide for oscillating said rear end of said receiving part.

11. The hand piece of claim 1, wherein said eccentric has a circular bore for oscillating said receiving part.

12. A dentistry hand piece comprising:

a neck portion having a longitudinal axis;

an attachment head connected to said neck portion, said attachment head including a receiving part for a tool, a drive member, and a rotation converter for converting a rotation of said drive member into an oscillation of said receiving part, said rotation converter including an eccentric driven by said drive member, said eccentric being connected to said receiving part;

wherein the oscillation of said receiving part lies exclusively in an imaginary plane perpendicular to a longitudinal axis of said receiving part; and wherein an angle is formed between the longitudinal axis of said receiving part and the longitudinal axis of said neck portion; and wherein said drive member comprises a compressed air-driven turbine in said attachment head.

13. A dentistry hand piece comprising:

a neck portion having a longitudinal axis;

an attachment head connected to said neck portion, said attachment head including a receiving part for a tool, a drive member, and a rotation converter for converting a rotation of said drive member into an oscillation of said receiving part;

wherein the oscillation of said receiving part lies exclusively in an imaginary plane perpendicular to a longitudinal axis of said receiving part;

wherein an angle is formed between the longitudinal axis of said receiving part and the longitudinal axis of said neck portion;

wherein said attachment head further includes a housing, said receiving part being elastically mounted within said housing; and wherein said rotation converter includes an unbalanced rotating part surrounding said receiving part.

14. The hand piece of claim 13, wherein said unbalanced rotating part comprises an unbalanced impeller of a compressed air-driven turbine.

15. The hand piece of claim 13, wherein said attachment head further includes a ball bearing between said unbalanced rotating part and said receiving part.

16. The hand piece of claim 13, wherein said attachment head further includes a first elastic element for elastically mounting a forward portion of said receiving part within said housing and a second elastic element for elastically mounting a rear portion of said receiving part within said housing, wherein said unbalanced rotating part is located between said first elastic element and said second elastic element.

17. The hand piece of claim 16, wherein said attachment head further includes a ball bearing, said ball bearing being located between said receiving part and said second elastic element or between said second elastic element and said housing.

18. A dentistry hand piece comprising:

a neck portion having a longitudinal axis;

an attachment head connected to said neck portion, said attachment head including a receiving part for a tool, a drive member, and a rotation converter for converting a rotation of said drive member into an oscillation of said receiving part, wherein the oscillation of said receiving part lies in an imaginary plane perpendicular to a longitudinal axis of said receiving part;

wherein said rotation converter includes an eccentric driven by said drive member, said eccentric being configured as a rotating sleeve having an eccentric bore, wherein a rear portion of said receiving part is mounted within said bore such that said receiving part is connected to said eccentric; and wherein an angle is formed between the longitudinal axis of said receiving part and the longitudinal axis of said neck portion.

* * * * *